US012656328B2

(12) United States Patent
Liberato et al.

(10) Patent No.: US 12,656,328 B2
(45) Date of Patent: Jun. 16, 2026

(54) ENVIRONMENTALLY SENSITIVE PLANT ID TAG

(71) Applicant: Temptime Corporation, Morris Plains, NJ (US)

(72) Inventors: Eric W. Liberato, Pequannock, NJ (US); Annika Matas Alonzo, West Hills, CA (US); Mohannad Abdo, Clifton, NJ (US)

(73) Assignee: ZEBRA TECHNOLOGIES CORPORATION, Lincolnshire, IL (US)

( * ) Notice: Subject to any disclaimer, the term of this patent is extended or adjusted under 35 U.S.C. 154(b) by 63 days.

(21) Appl. No.: 18/374,973

(22) Filed: Sep. 29, 2023

(65) Prior Publication Data

US 2025/0110104 A1 Apr. 3, 2025

(51) Int. Cl.
| | |
|---|---|
| *G01N 33/24* | (2006.01) |
| *G01N 21/78* | (2006.01) |
| *G01N 27/22* | (2006.01) |
| *H04B 5/73* | (2024.01) |

(52) U.S. Cl.
CPC ........... *G01N 33/246* (2013.01); *G01N 21/78* (2013.01); *G01N 27/223* (2013.01); *H04B 5/73* (2024.01)

(58) Field of Classification Search
CPC .............................. G01N 33/246; G01N 21/78
USPC ...................................................... 340/539.26
See application file for complete search history.

(56) References Cited

U.S. PATENT DOCUMENTS

| | | | | | |
|---|---|---|---|---|---|
| 3,019,638 | A | * | 2/1962 | Klein | ................... G01N 31/222 D10/56 |
| 3,951,098 | A | * | 4/1976 | Meyers | .................. G01N 21/29 73/73 |
| 4,020,785 | A | * | 5/1977 | Palmer | ................. A01G 25/167 116/200 |
| 4,201,080 | A | * | 5/1980 | Slepak | ................. A01G 25/167 73/73 |
| 8,009,048 | B2 | * | 8/2011 | Hyde | ..................... A01G 9/006 47/1.01 R |
| 8,258,951 | B2 | * | 9/2012 | Hyde | ..................... A01G 9/006 340/572.1 |

(Continued)

FOREIGN PATENT DOCUMENTS

| | | | | |
|---|---|---|---|---|
| DE | 202005005976 | U1 * | 10/2005 | ........... A01G 25/167 |
| DE | 102013004025 | A1 * | 9/2013 | ........... G01N 27/048 |

(Continued)

*Primary Examiner* — Eric Blount
(74) *Attorney, Agent, or Firm* — K&L Gates LLP

(57) ABSTRACT

Environmentally sensitive plant ID tags are disclosed herein. An example environmentally sensitive tag for use in a plant growing medium, includes; a substrate including a tag insertion end which is narrowed, pointed, or rounded; an indicator located on or in the substrate, the indicator having an initial state and at least one activated state, the indicator configured to transition from the initial state to the at least one activated state in response to exposure to moisture producing an observable change; and a wicking material disposed longitudinally along or in the substrate, from an area of the substrate proximate the tag insertion end to the indicator and configured to conduct moisture from the growing medium to the indicator when the tag insertion end is inserted in the plant growing medium.

23 Claims, 9 Drawing Sheets

(56) References Cited

U.S. PATENT DOCUMENTS

| | | | | | |
|---|---|---|---|---|---|
| 8,258,952 | B2 * | 9/2012 | Hyde | .................... | A01G 9/006 |
| | | | | | 340/572.1 |
| 8,279,066 | B2 * | 10/2012 | Hyde | ...................... | H04B 5/48 |
| | | | | | 47/1.01 R |
| 8,284,058 | B2 * | 10/2012 | Hyde | ................... | A01G 25/167 |
| | | | | | 340/572.1 |
| 8,305,214 | B2 * | 11/2012 | Hyde | .................... | A01G 9/006 |
| | | | | | 47/1.01 R |
| 8,373,563 | B2 * | 2/2013 | Hyde | ...................... | H04Q 9/00 |
| | | | | | 340/572.1 |
| 8,997,682 | B1 * | 4/2015 | Ashcroft | ............... | G01N 21/29 |
| | | | | | 116/200 |
| 10,095,972 | B2 * | 10/2018 | Bhatia | ............. | G06K 19/07745 |
| 10,140,566 | B2 * | 11/2018 | Viikari | .................... | H04Q 9/00 |
| 11,435,294 | B2 * | 9/2022 | Abdo | ..................... | C09D 11/50 |
| 2006/0261946 | A1 * | 11/2006 | Himberger | ......... | G06K 19/0717 |
| | | | | | 340/572.1 |
| 2008/0078233 | A1 * | 4/2008 | Larson | ................ | G01N 29/022 |
| | | | | | 73/335.03 |
| 2016/0123867 | A1 * | 5/2016 | Orihara | ................. | G01N 19/10 |
| | | | | | 73/73 |
| 2022/0349821 | A1 * | 11/2022 | Peters | ................... | G01N 21/81 |
| 2023/0274117 | A1 * | 8/2023 | O'Bryan | ............. | G06K 7/0008 |
| | | | | | 340/572.1 |
| 2024/0027385 | A1 * | 1/2024 | Huffman | ............. | G01N 27/221 |

FOREIGN PATENT DOCUMENTS

| | | | | | |
|---|---|---|---|---|---|
| EP | 2949201 | A1 * | 12/2015 | ....... | A01G 19/07718 |
| FR | 3021746 | A1 * | 12/2015 | ........... | A01G 27/008 |
| WO | WO-2016059285 | A1 * | 4/2016 | ....... | G06K 19/07718 |
| WO | WO-2023065015 | A1 * | 4/2023 | ............... | C09J 5/06 |

* cited by examiner

ENVIRONMENTALLY SENSITIVE PLANT ID TAG

BACKGROUND

In gardening and farming, plant tags are used for identification purposes, and separate instruments and techniques are used for determining soil moisture content.

SUMMARY

The devices of the present disclosure comprise environmentally sensitive plant identification tags, capable of indicating soil moisture and humidity in addition to plant identification.

In a first embodiment of the present disclosure, an environmentally sensitive tag for use in a plant growing medium is provided. The environmentally sensitive tag includes a substrate having a tag insertion end which is narrowed, pointed, or rounded to facilitate insertion of the tag insertion end in the plant growing medium; an indicator located on or in the substrate and spaced away from the tag insertion end, the indicator having an initial state and at least one activated state, the indicator configured to transition from the initial state to the at least one activated state in response to exposure to moisture producing an observable change; and a wicking material disposed longitudinally along or in the substrate, from an area of the substrate proximate the tag insertion end to the indicator and configured to conduct moisture from the plant growing medium to the indicator when the tag insertion end is inserted in the plant growing medium.

In a first variation of this embodiment, a change from the initial state to the activated state occurs in response to exposure of the indicator to a predetermined moisture level threshold greater than about 10% Relative Humidity (RH), about 20% RH, about 30% RH, about 40% RH, about 50% RH, about 60% RH, about 70% RH, about 80% RH, about 90% RH, or about 100% RH.

In a second variation of this embodiment the indicator has a plurality of activated states each associated with a respective moisture level threshold, the indicator entering each successive activated states in response to exposure to a respective moisture greater than the respective moisture level threshold.

In a third variation of this embodiment each of the plurality of activated states has a corresponding observable change that is distinguishable from the other states.

In a fourth variation of this embodiment the observable change of the indicator from the initial state to the activated state is not reversed when a moisture level returns below the predetermined moisture level threshold.

In a fifth variation of this embodiment the indicator is reversible, so that when the indicator is in the activated state, the indicator is operable to revert from the activated state to the initial state in response to a moisture level falling below a predetermined minimum threshold.

In a sixth variation of this embodiment the indicator further includes a hydrochromic ink, and the observable change includes a change in a color state of the hydrochromic ink, wherein the change in color state includes a change of at least one property chosen from the group consisting of hue, chroma, transparency, opacity, and combinations thereof.

In a seventh variation of this embodiment the hydrochromic ink forms an indicia that is visible when the indicator is in the initial state and which becomes invisible when the indicator transitions to the at least on activated state; or is invisible when the indicator is in the initial state and which becomes visible when the indicator transitions to the at least one activated state.

In an eighth variation of this embodiment, the tag further includes a plurality of different hydrochromic inks, each hydrochromic ink having a respective moisture level threshold and a respective observable change when the indicator is exposed to a moisture level above the respective moisture level threshold.

In a ninth variation of this embodiment the hydrochromic ink passes through a series of color states in response to different humidity levels, where each color state corresponds to a respective activated state of the plurality of activated states.

In a tenth variation of this embodiment the hydrochromic ink includes at least one component chosen from the list consisting of a mixture of a triphenylmethane dye, an oxidizing agent, a base and a humectant; a mixture of an inorganic weak acid, a triarylmethane dye, and a hygroscopic agent; a mixture of copper bromide, a dye and a bromide salt; a silica gel impregnated iron (III) salt; a sugar gel containing ionic dyes; a composite of porphyrin, magnesium dichloride and silica gel; an inorganic polymer containing an acid-base indicator; hydroxyethyl cellulose containing methylene blue and urea; a composite of polyvinyl alcohol and sodium borate decahydrate; lithium hydroxide; calcium hydroxide; potassium hydroxide; sodium hydrogen carbonate; magnesium hydroxide; sodium thiosulfate pentahydrate; sodium hydroxide; cobalt nitrate; copper (II) sulfate; copper nitrate; iron (III) sulfate; iron (II) sulfate; iron (II) Chloride; iron (III) chloride; Cobalt (II) Chloride; or magnesium chloride.

In an eleventh variation of this embodiment the indicator further includes a component that changes an electrical property when it transitions from the initial state to the at least one activated state.

In a twelfth variation of this embodiment the indicator further includes an RFID tag which includes or is electrically connected to the component, wherein the RFID tag is configured to change its output in response to the change in the electrical property of the component.

In a thirteenth variation of this embodiment the change in the electrical property of the component includes a change in capacitance.

In a fourteenth variation of this embodiment the change in capacitance increases with greater exposure to moisture.

In a fifteenth variation of this embodiment the change in capacitance causes a change in a frequency of a transmission of the RFID tag.

In a sixteenth variation of this embodiment the RFID tag and the wicking material are disposed inside the substrate or between the substrate and a second layer or inside of the substrate, so that the wicking material and RFID tag are substantially insulated from moisture contact, except for moisture which is transmitted from the tag insertion end through the wicking material.

In a seventeenth variation of this embodiment the wicking material includes at least one component from a list consisting of woven polyester, nonwoven polyester, polyamide and blended elastane and polyester, carbon fiber, Teslin synthetic paper, polyethylene, polypropylene, polytetrafluoroethylene, and woven nylon.

In an eighteenth variation of this embodiment the substrate is formed entirely or in part by the wicking material.

A nineteenth variation of this embodiment further includes additional material which is a same material as the substrate, at least partially surrounding the environmentally sensitive tag, and which is connected to the substrate by a line of weakness.

In a second embodiment, the present invention is an article of manufacture, comprising a plurality of environmentally sensitive tags of claim 1 forming a connected web or sheet.

In a first variation of this embodiment adjacent environmentally sensitive tags in the connected web or sheet have a line of weakness along a boundary in between the adjacent environmentally sensitive tags.

In a second variation of this embodiment the line of weakness is selected from the group consisting of a fold, a score line, and a perforated line.

BRIEF DESCRIPTION OF THE DRAWINGS

The accompanying figures, where like reference numerals refer to identical or operationally similar elements throughout the separate views, together with the detailed description below, are incorporated in and form part of the specification, and serve to further illustrate embodiments of concepts that include the claimed invention, and explain various principles and advantages of those embodiments.

Figure 1:
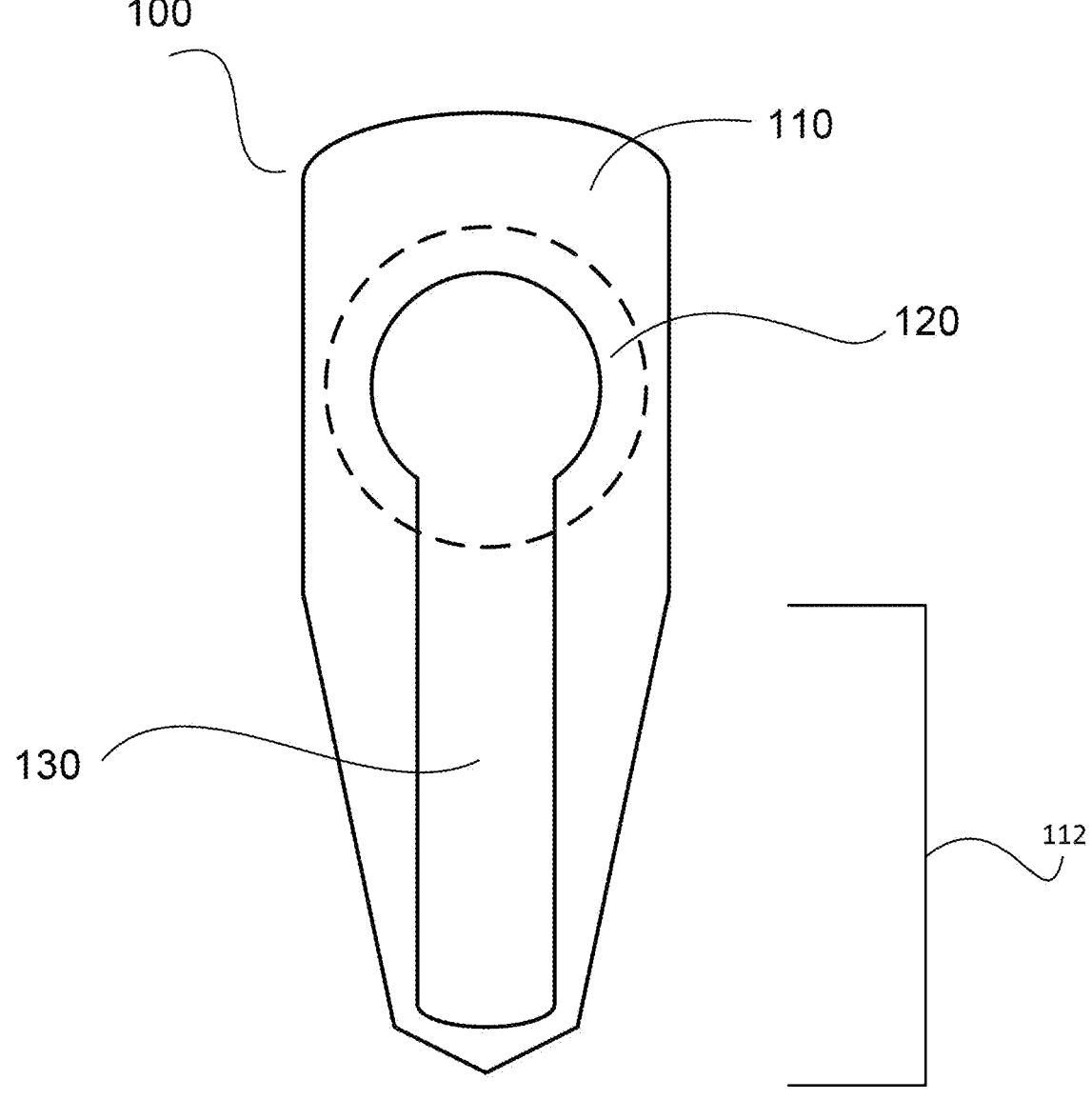
FIG. 1 depicts an example embodiment of an environmentally sensitive plant tag with a hydrochromic ink indicia.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

FIG. 1 illustrates an environmentally sensitive plant ID tag with a hydrochromic ink indicia, according to embodiments of the present disclosure. The hydrochromic tag 100 comprises a substrate 110, a hydrochromic indicium 120 and a wicking material 130. In some examples, the substrate has an insertion end 112 to be inserted into the growing medium of the plant. The wicking material 130 is disposed longitudinally along the substrate 110, or in the substrate 110, parallel with the direction of insertion. As the hydrochromic tag 100 is inserted into a growing medium, the wicking material 130 draws moisture up that tag from the insertion end 112 to the hydrochromic indicium 120. The hydrochromic indicium 120 reacts with the moisture introduced by the wicking material 130, and the indicium changes from an initial state to an activated state.

According to some embodiments, the hydrochromic indicium 120 comprises a hydrochromic ink that changes color respondent to contact with liquid water. In such embodiments, the wicking material 130 must draw sufficient moisture from the growing medium up into the tag to introduce liquid water to the hydrochromic indicium 120 in order to induce the activated state, reflected by a change in color state. The distance that water is able to travel up the wicking material 130 by capillary action is proportional to the volumetric proportion of water in the soil, water by volume (WBV). By varying the length of the wicking material 130, referential to the location of the hydrochromic indicium 120 and the insertion end 112, the hydrochromic tag 100 can be configured to indicate a different volumetric ratio of water content in the growing medium.

According to some embodiments, the change in color state of the hydrochromic indicium 120 includes changes in properties such as hue, chroma, transparency, opacity and combinations thereof.

In some examples, the hydrochromic tag 100 can be configured to respond to a first WBV threshold of about 5% WBV, about 10% WBV, about 15% WBV, about 20% WBV, about 25% WBV, about 30% WBV, about 35% WBV, about 40% WBV, about 45% WBV, about 50% WBV, about 55% WBV, or about 60% WBV in the growing medium.

In some examples, the wicking material 130 may include woven polyester, nonwoven polyester, polyamide and blended elastane and polyester, carbon fiber, Teslin synthetic paper, polyethylene, polypropylene, polytetrafluoroethylene, woven nylon, or any material suitable to draw water from a medium by capillary action.

In some examples, the hydrochromic ink used in the hydrochromic indicia 120 is a mixture of a triphenylmethane dye, an oxidizing agent, a base and a humectant, or a mixture of an inorganic weak acid, a triarylmethane dye, and a hygroscopic agent. In other examples the hydrochromic ink is a mixture of copper bromide, a dye and a bromide salt. In yet other examples, the hydrochromic ink is a silica gel impregnated iron (III) salt, a sugar gel containing ionic dyes, or a composite of porphyrin, magnesium dichloride and silica gel. In some examples, the hydrochromic ink is an inorganic polymer containing an acid-base indicator, hydroxyethyl cellulose containing methylene blue and urea, or a composite of polyvinyl alcohol and sodium borate decahydrate. In some examples the hydrochromic ink used in the hydrochromic indicia 120 may be any suitable compound exhibiting a color change responsive to contact with liquid water.

According to some embodiments, the hydrochromic tag 100 may include a plurality of hydrochromic indicia 120 disposed along the length of the wicking material, such that multiple levels of soil moisture can be indicated progressively as moisture travels up the wicking material 130. In some examples, the hydrochromic tag may be configured to progressively indicate about 20% WBV, about 30% WBV and about 40% WBV.

According to another embodiment, the hydrochromic indicium 120 includes an applied compound capable of forming hydrates that have a different color from the non-hydrated form of the compound. The compound may be chosen and/or configured to form a certain amount of the hydrated compound respondent to a certain level of relative humidity (RH), thus as a predetermined % RH is reached in the environment, the compound may form an amount of hydrate sufficient to incur a color change visible to the naked eye.

In some examples, the hydrochromic indicium 120 may be configured to respond to a first humidity value around or above 40% RH, around or above 50% RH, around or above 60% RH, around or above 70% RH, or around or above 80% RH. In some examples, the hydrochromic indicium 120 may be configured to respond to a first humidity value in a range of from about 40% to about 45% RH, about 45% to about 50% RH, about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, or any combinations thereof. In other examples, the hydrochromic indicium 120 may be configured to respond to any other suitable humidity value (e.g., between 0% RH to 40% RH). In some examples, the hydrochromic indicium 120 may be configured to respond to a first humidity value around or above 40% RH, around or above 50% RH, around or above 60% RH, around or above 70% RH, or around or above 80% RH. In some examples, the hydrochromic indicium 120 may be configured to respond to a first humidity value in a range of from about 40% to about 45% RH, about 45% to about 50% RH, about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, or any combinations thereof. In other examples, the hydrochromic indicium 120 may be configured to respond to any other suitable humidity value (e.g., between 0% RH to 40% RH).

In some examples, the applied compound may include one or more of lithium hydroxide; calcium hydroxide; potassium hydroxide; sodium hydrogen carbonate; magnesium hydroxide; sodium thiosulfate pentahydrate; sodium hydroxide; cobalt nitrate; copper (II) sulfate; copper nitrate; iron (III) sulfate; iron (II) sulfate; iron (II) Chloride; iron (III) chloride; Cobalt (II) Chloride; or magnesium chloride.

In some examples, the hydrochromic indicia 120 may be fully or partially printed on a rigid or flexible substrate 110, for example, by screen printing, gravure, flexographic, ink jet, or slot die coating. In other examples, the hydrochromic indicia 120 may be printed using any other suitable printing methods.

According to some embodiments, the hydrochromic tag 100 may include a plurality of hydrochromic indicia 120, each containing a differing configuration of applied component, such that each indicium is tuned to indicate a higher level of relative humidity. As relative humidity increases, more indicia are activated.

In some examples, the hydrochromic indicium 120 may have a plurality of activated states, such that the hydrochromic indicium 120 exhibits multiple state changes in response to progressively greater exposures to moisture.

In some examples, the change from the initial state to the activated state of the hydrochromic indicium 120 is irreversible. That is, after the hydrochromic indicium 120 was exposed to a high humidity (e.g., 75% relative humidity (RH)), although it returns to an initial humidity (e.g., from 75% RH to 40% RH), the hydrochromic indicium 120 may remain in the activated state (e.g., measured at 75% RH) or may not return to its initial state (e.g., measured at 40% RH before the exposure to the high humidity). In such examples, the hydrochromic ink or hydrochromic compound may be undergoing a one-way or irreversible change in response to the environmental stimulus.

In some examples, the change from the initial state to the activated state may be considered irreversible when the state change persists or does not return to its initial state after exposure for at least 48 hours to the initial humidity, such as after exposure for at least 72 hours to the initial humidity, after exposure for at least 120 hours to the initial humidity, or after exposure for at least 168 hours to the initial humidity.

In some examples, the change from the initial state to the activated state of the hydrochromic indicium 120 is reversible. That is, after the hydrochromic indicium 120 returns to an initial humidity, the hydrochromic indicium 120 may not remain in the activated state. For example, after the hydrochromic indicium 120 returns to the initial humidity, the hydrochromic indicium 120 reverts to the initial state with the first color.

In some cases, the change in state may be considered reversible when the changed state does not persist or when the changed state returns to the initial state after exposure for 168 hours (a week) or less to the initial humidity. For example, the subsequent exposure to the initial humidity may be for about 1 minute to about 168 hours, such as for about 1 minute to about 2 minutes, for about 2 minutes to about 5 minutes, for about 5 minutes to about 10 minutes, for about 10 minutes to about 30 minutes, for about 30 minutes to about 1 hour, for about 1 hour to about 2 hours, for about 2 hours to about 5 hours, for about 5 hours to about 10 hours, for about 10 hours to about 24 hours, for about 24 hours to about 48 hours, for about 48 hours to about 72 hours, for about 72 hours to about 120 hours, or for about 120 hours to about 168 hours.

In some examples, the substrate 110 may be made with a paper or polyethylene terephthalate (PET). In other examples, the substrate 105 may be made with any other suitable non-conductive material or any breathable film, such as cloth or plastic (e.g., polyethylene terephthalate (PET), polyvinyl chloride (PVC), polyvinyl acetate (PVAC), etc.).

According to some embodiments, the wicking material 130 may be formed such that the substrate 110 is partially or entirely composed of the wicking material 130.

According to some embodiments, the hydrochromic indicia 120 may be accompanied by a reference area on the substrate 110. For example, the indicia may be surrounded by a reference area printed with the color corresponding to the activated state, such that when the hydrochromic tag 100 changes from the initial state to the activated state, the hydrochromic indicium and the reference area appear monochromatic, and when the moisture level is insufficient to incite a state change from the initial state to the activated state, or when the moisture level has dropped from a previous higher level to a low level, and the hydrochromic indicium 120 reverts from the activated state to the initial state, the hydrochromic indicium 120 and the reference area are different colors, so as to draw attention to an insufficient moisture level.

In other examples, the reference area may be the same color as the initial state, such that when the hydrochromic indicia 120 transitions to the activated state in response to the presence of moisture, the hydrochromic indicium becomes visually distinct from the reference area.

In some examples, the hydrochromic indicium 120 may be configured to form a symbol or natural language text. For example, in an initial state, the hydrochromic indicium 120 could form the phrase "water me," indicating a low soil moisture level, and in the activated state the hydrochromic indicium, being a second color, would be chromatically matched with the reference area and no message would be visible, indicating that there is not a need to add water to the growing medium.

In some examples, the reference area includes a partial or complete surface area of the substrate 110.

In some examples, the substrate 110 also includes media, printed or otherwise, that provides information about a plant which it is designed to accompany. This media may include the name of a plant or plants, care instructions, ideal moisture or humidity levels, and other information pertinent to the cultivation of the plant.

Figure 2A:
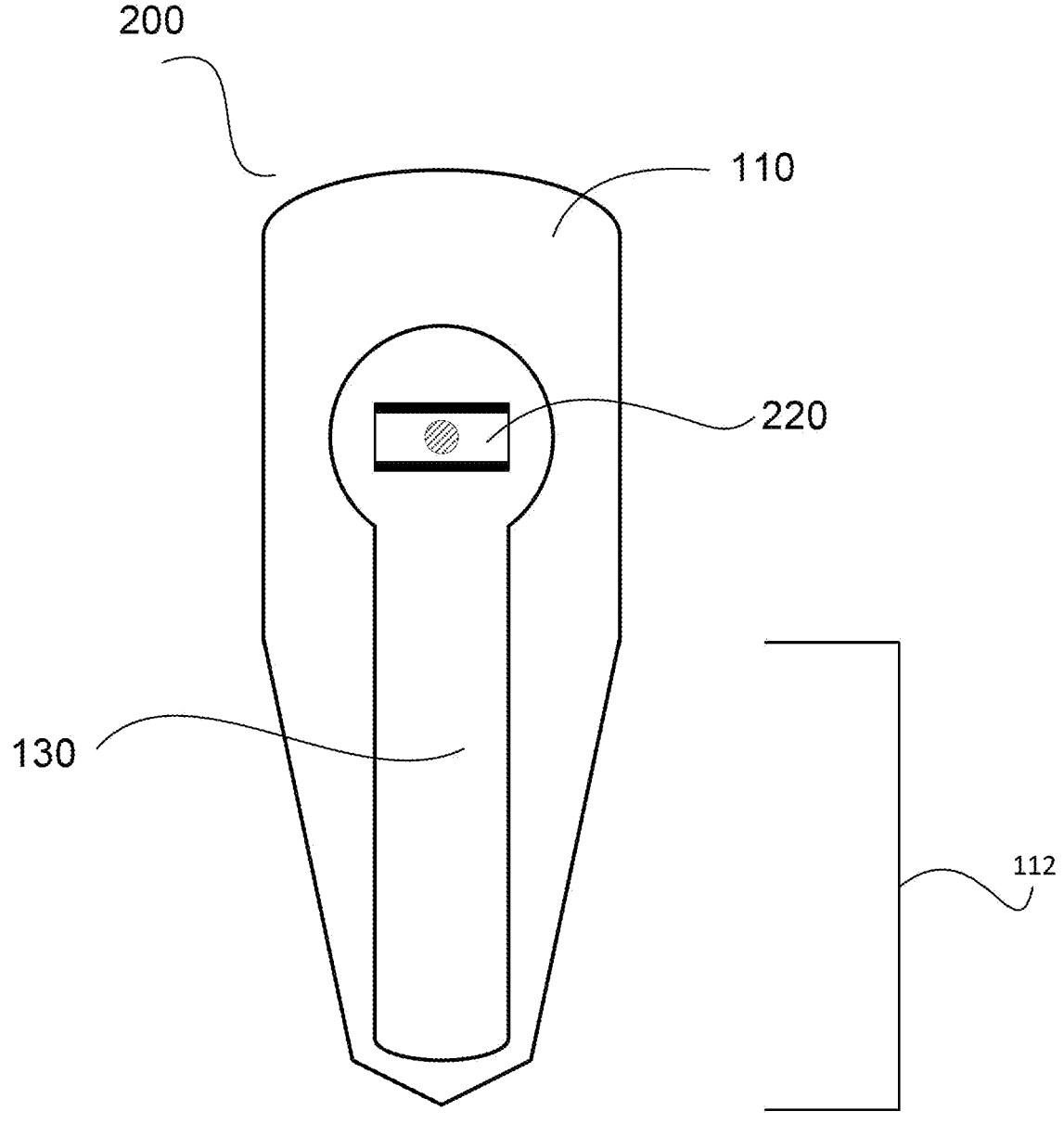
FIG. 2A depicts an example embodiment of an environmentally sensitive plant tag with an RFID indicator.

FIG. 2A illustrates an environmentally sensitive plant ID tag with an RFID indicator, according to embodiments of the present disclosure. The RFID tag 200 has a substrate 110 with an insertion end 112 and a wicking material 130. The indicator of the RFID tag is an RFID chip 220 that contains a component configured to change an electrical property when moisture contacts the component. The change in the electrical property of the component is reflected by a change in the frequency of the transmissions of the RFID chip 220 and/or a change in data included in the transmissions of the RFID chip 220.

In some examples, the electrical property that exhibits a change when exposed to moisture is capacitance or resistance.

In some examples, a first threshold capacitance value may correspond to a first humidity value around or above 40% RH, around or above 50% RH, around or above 60% RH, around or above 70% RH, or around or above 80% RH. In some examples, the first threshold capacitance value may correspond to a first humidity value in a range of from about 40% to about 45% RH, about 45% to about 50% RH, about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, or any combinations thereof. In other examples, the first threshold capacitance value may correspond to any other suitable humidity value (e.g., between 0% RH to 40% RH). In some examples, the first threshold capacitance value may correspond to a first humidity value around or above 40% RH, around or above 50% RH, around or above 60% RH, around or above 70% RH, or around or above 80% RH. In some examples, the first threshold capacitance value may correspond to a first humidity value in a range of from about 40% to about 45% RH, about 45% to about 50% RH, about 50% to about 55% RH, from about 55% to about 60% RH, from about 60% to about 65% RH, from about 65% to about 70% RH, from about 70% to about 75% RH, from about 75% to about 80% RH, from about 80% to about 85% RH, from about 85% to about 90% RH, or any combinations thereof. In other examples, the first threshold capacitance value may correspond to any other suitable humidity value (e.g., between 0% RH to 40% RH).

In some examples, the RFID chip 220 may have a first capacitance value before exposure to the humidity above the threshold/target humidity, and a second capacitance value after exposure to the humidity above the threshold/target humidity. The second capacitance may be greater than the first capacitance. In some examples, the first capacitance value may be in a range of 5 pF to 10 pF, 10 pF to 15 pF, 15 pF to 20 pF, or any combinations thereof. In some examples, the second capacitance value may be equal to or greater than 10 pF, for example, in a range of from about 10 pF to about 20 pF, from about 15 pF to about 50 pF, from about 50 pF to about 1000 pF, greater than about 1000 pF, or any combinations thereof. In other examples, the first and second capacitance values may have any other suitable capacitance value. In some examples, the difference between the first capacitance value and the second capacitance value may be in a range of about 2 pF to about 3000 pF, for example, from about 2 pF to about 10 pF, from about 10 pF to about 20 pF, from about 20 pF to about 50 pF, from about 50 pF to about 100 pF, from about 100 pF to about 1000 pF, from about 1000 pF to about 3000 pF, greater than 3000 pF, or any combinations thereof.

In some examples, the change in capacitance of the RFID chip 220 is irreversible. That is, after the RFID chip 220 was exposed to a high humidity (e.g., 75% relative humidity (RH)), although it returns to an initial humidity (e.g., from 75% RH to 40% RH), the RFID chip 220 may retain the changed capacitance value (e.g., measured at 75% RH) or may not return to its initial capacitance value (e.g., measured at 40% RH before the exposure to the high humidity).

In some examples, the change in capacitance may be considered irreversible when the changed capacitance persists or does not return to its initial capacitance value after exposure for at least 48 hours to the initial humidity, such as after exposure for at least 72 hours to the initial humidity, after exposure for at least 120 hours to the initial humidity, or after exposure for at least 168 hours to the initial humidity.

In some examples, the change in capacitance of the RFID chip 220 is reversible. That is, after the RFID chip 220 returns to an initial humidity, the RFID chip 220 may not retain the changed capacitance value. For example, after the RFID chip 220 returns to the initial humidity, the capacitance value of the RFID chip 220 may return to its initial capacitance value or a capacitance value close to the initial capacitance value.

In some cases, the change in capacitance may be considered reversible when the changed capacitance does not persist or when the changed capacitance returns to the initial capacitance value after exposure for 168 hours (a week) or less to the initial humidity. For example, the subsequent exposure to the initial humidity may be for about 1 minute to about 168 hours, such as for about 1 minute to about 2 minutes, for about 2 minutes to about 5 minutes, for about 5 minutes to about 10 minutes, for about 10 minutes to about 30 minutes, for about 30 minutes to about 1 hour, for about 1 hour to about 2 hours, for about 2 hours to about 5 hours, for about 5 hours to about 10 hours, for about 10 hours to about 24 hours, for about 24 hours to about 48 hours, for about 48 hours to about 72 hours, for about 72 hours to about 120 hours, or for about 120 hours to about 168 hours.

In some examples, the change in capacitance of the RFID chip 220 may occur after its exposure to a change in humidity above a first threshold change value for a first predetermined amount of time. In some examples, the change in capacitance of the RFID chip 220 may occur after its exposure to a change in humidity below a second threshold change value for a second predetermined amount of time.

In some examples the RFID tag 200 indicates a moisture level when interrogated by a second device.

Some embodiments may employ a humidity sensing RFID chip similar to those described in U.S. patent application Ser. No. 17/867,031.

Figure 2B:
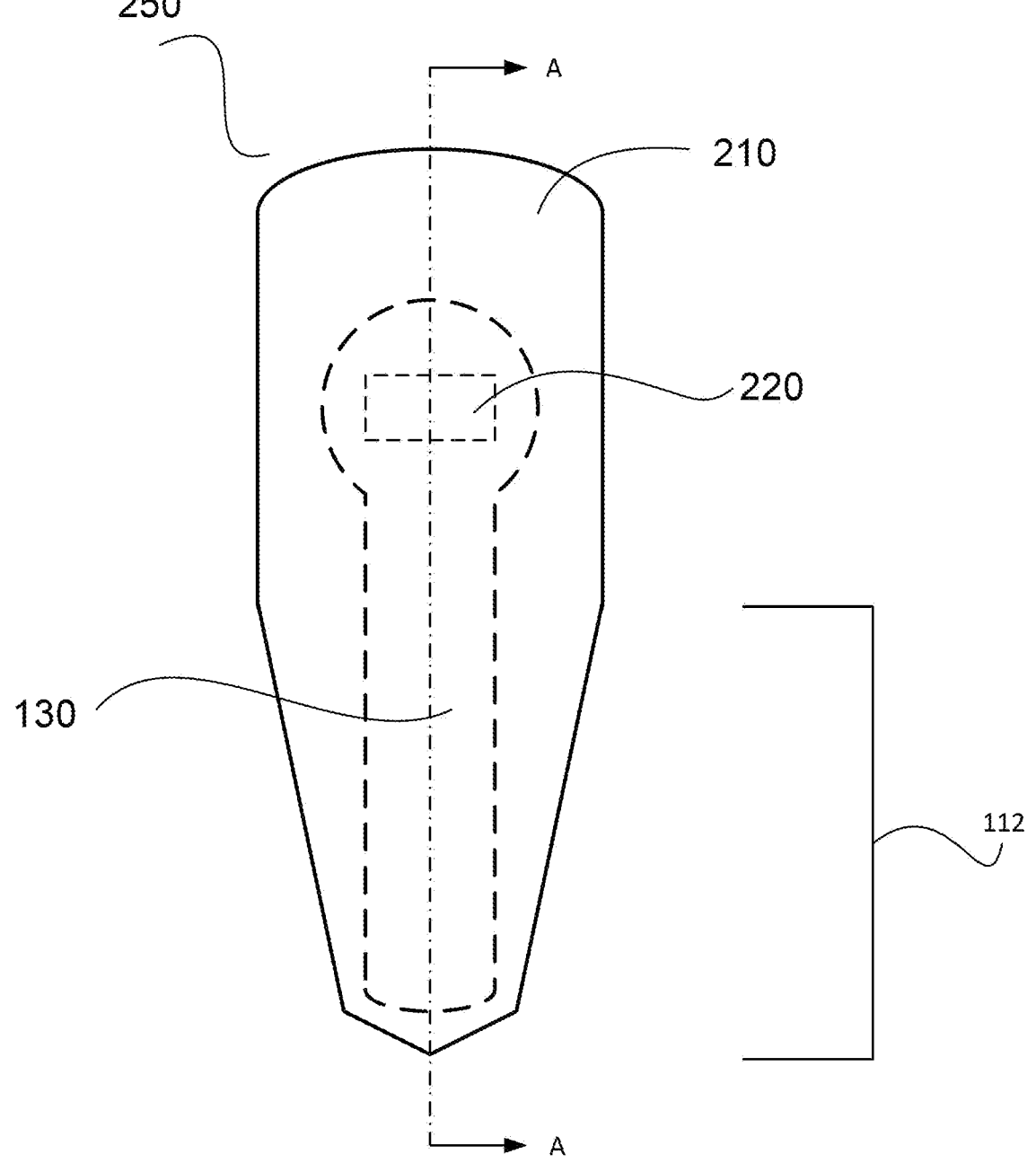
FIG. 2B depicts an example embodiment of an enclosed environmentally sensitive plant tag with an RFID indicator.

FIG. 2B illustrates an environmentally sensitive plant ID tag with an enclosed RFID indicator, according to embodiments of the present disclosure. Like the RFID tag 200 of FIG. 2, the enclosed RFID tag 250 has the substrate 110 (not viewable in FIG. 2B), the wicking material 130 and the RFID chip 220. The enclosed RFID tag 250 has a cover layer 210, dimensionally matched with the substrate 110 to encapsulate the wicking material and the RFID chip 220 between the substrate 110 and the core layer 210, such that the wicking material 130 and the RFID chip 220 are protected from outside elements, the wicking material 130 being exposed at the insertion end 112 (e.g., the core later 210 does not cover the wicking material 130 proximate to the insertion end). The cover layer 210 prevents the RFID chip 220 from responding to outside moisture, and ensures that the RFID chip 220 is respondent only to moisture introduced via the wicking material 130.

Figure 2C:
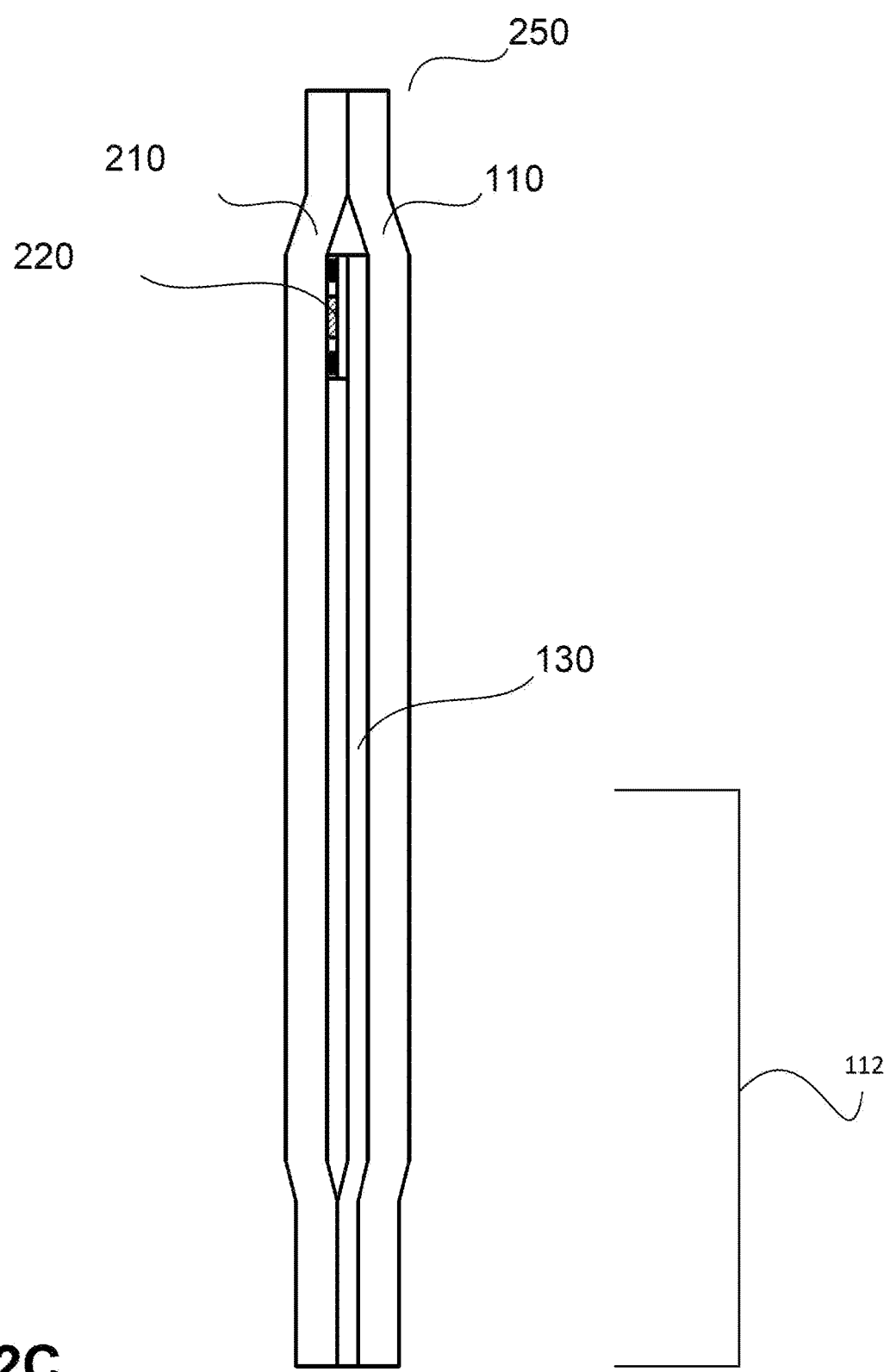
FIG. 2C depicts a cross section of the example embodiment of the enclosed environmentally sensitive plant tag with an RFID indicator of FIG. 2B along the line A-A.

FIG. 2C illustrates a cross sectional view of the enclosed RFID tag 250, as seen in FIG. 2B, taken along the line A-A, in which certain features are more easily viewed. The substrate 110 and the cover layer 210 are sealed at the edges of the non-insertion portion of the tag, and the wicking material 130 is exposed at the insertion end 112 of the enclosed RFID tag 250.

Figure 2D:
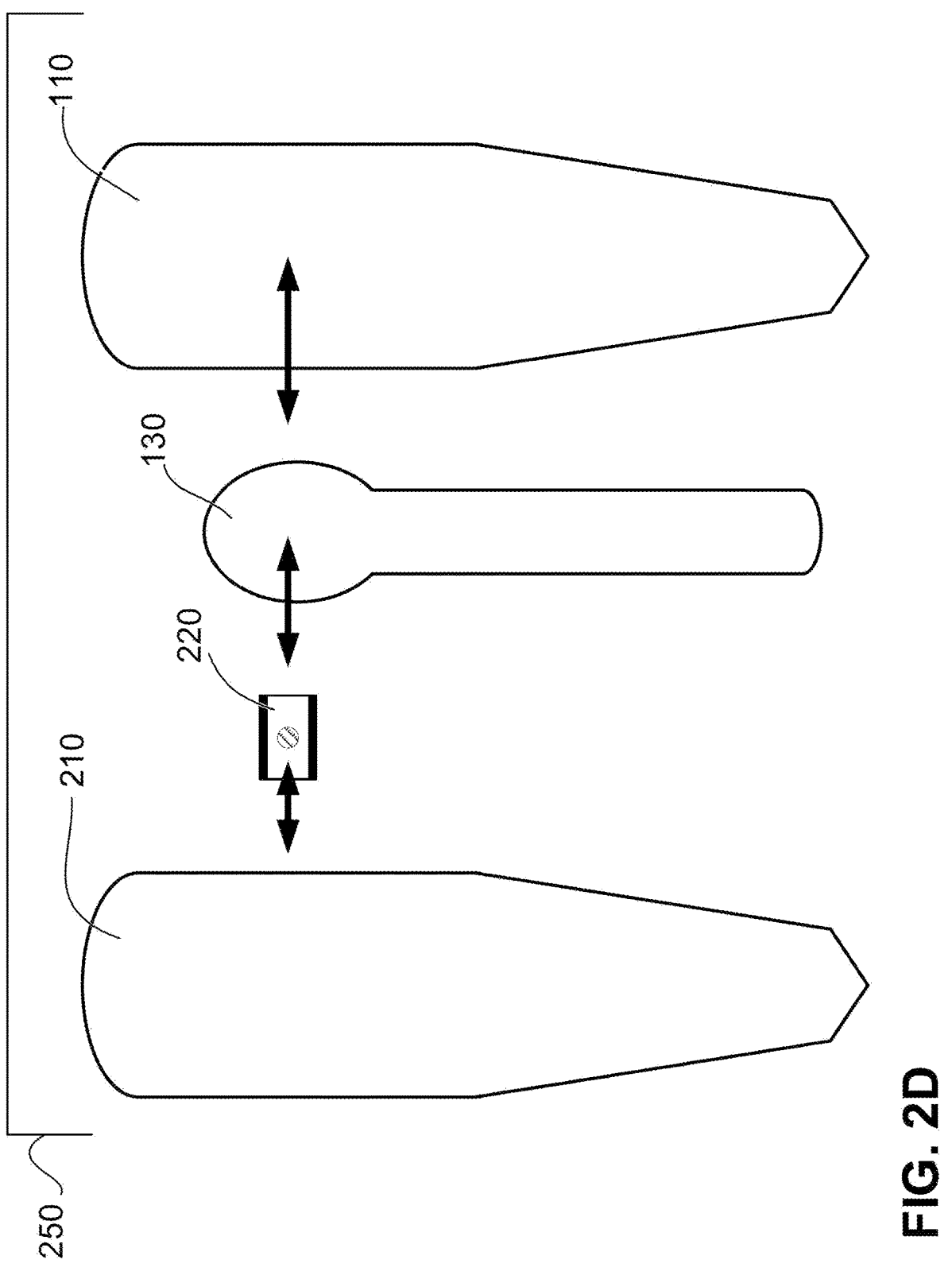
FIG. 2D depicts an exploded view of the example embodiment of the enclosed environmentally sensitive plant tag with an RFID indicator of FIG. 2B.

FIG. 2D illustrates an exploded view of the enclosed RFID tag 250, as seen in FIGS. 2B-C, wherein certain features are more easily viewed.

Figure 3:
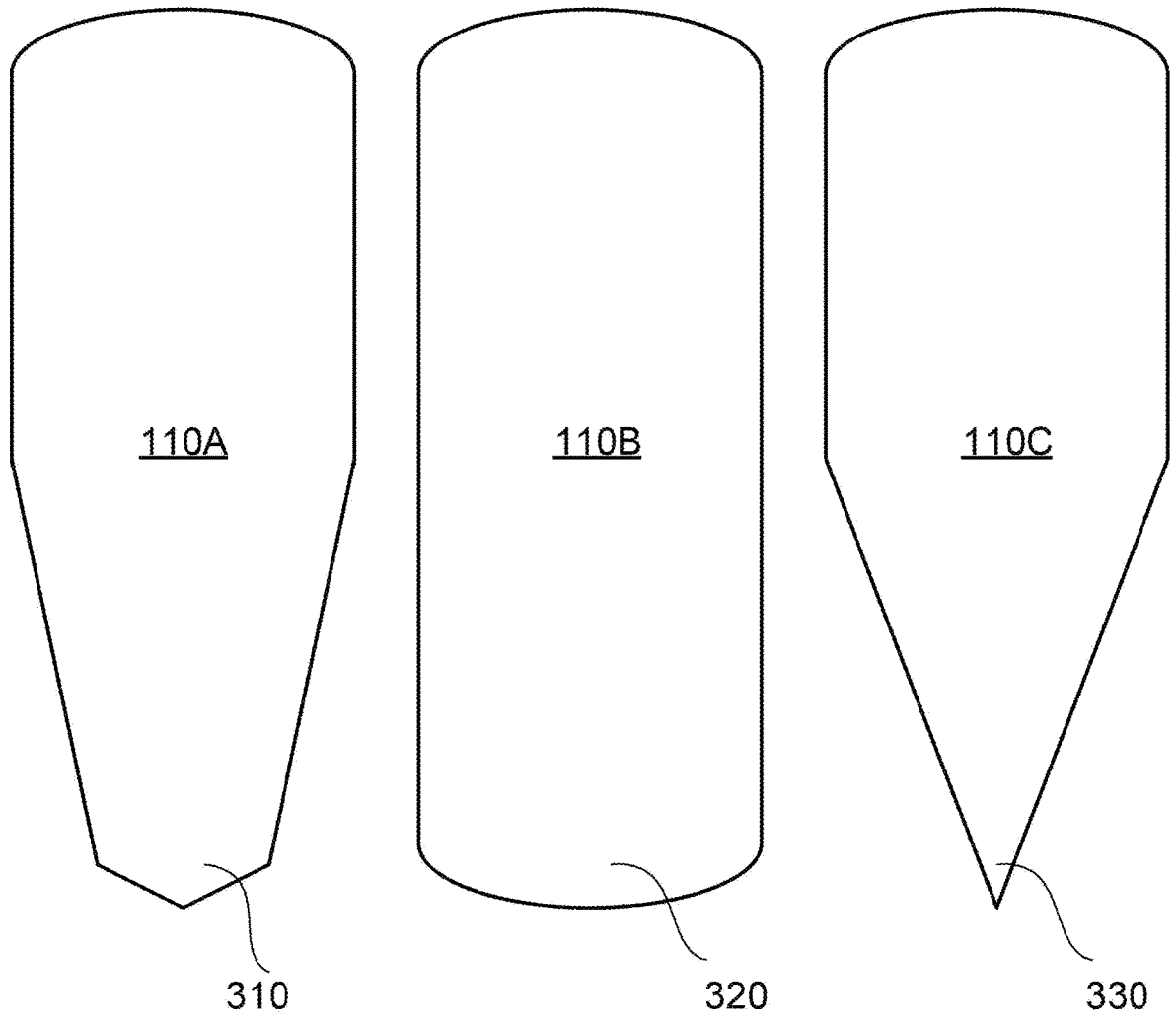
FIG. 3 depicts example embodiments of a substrate of an environmentally sensitive plant tag.

FIG. 3 illustrates multiple embodiments of the substrate 110. FIG. 3 illustrates a narrowed substrate 110A having a narrowed insertion end 310, a rounded substrate 110B having a rounded insertion end 320, and a pointed substrate 110C having a pointed insertion end 330, each of which may facilitate insertion of the tag into soil or another growing medium. It will be appreciated that other shapes that are suitable for a particular application may also be used.

Figure 4:
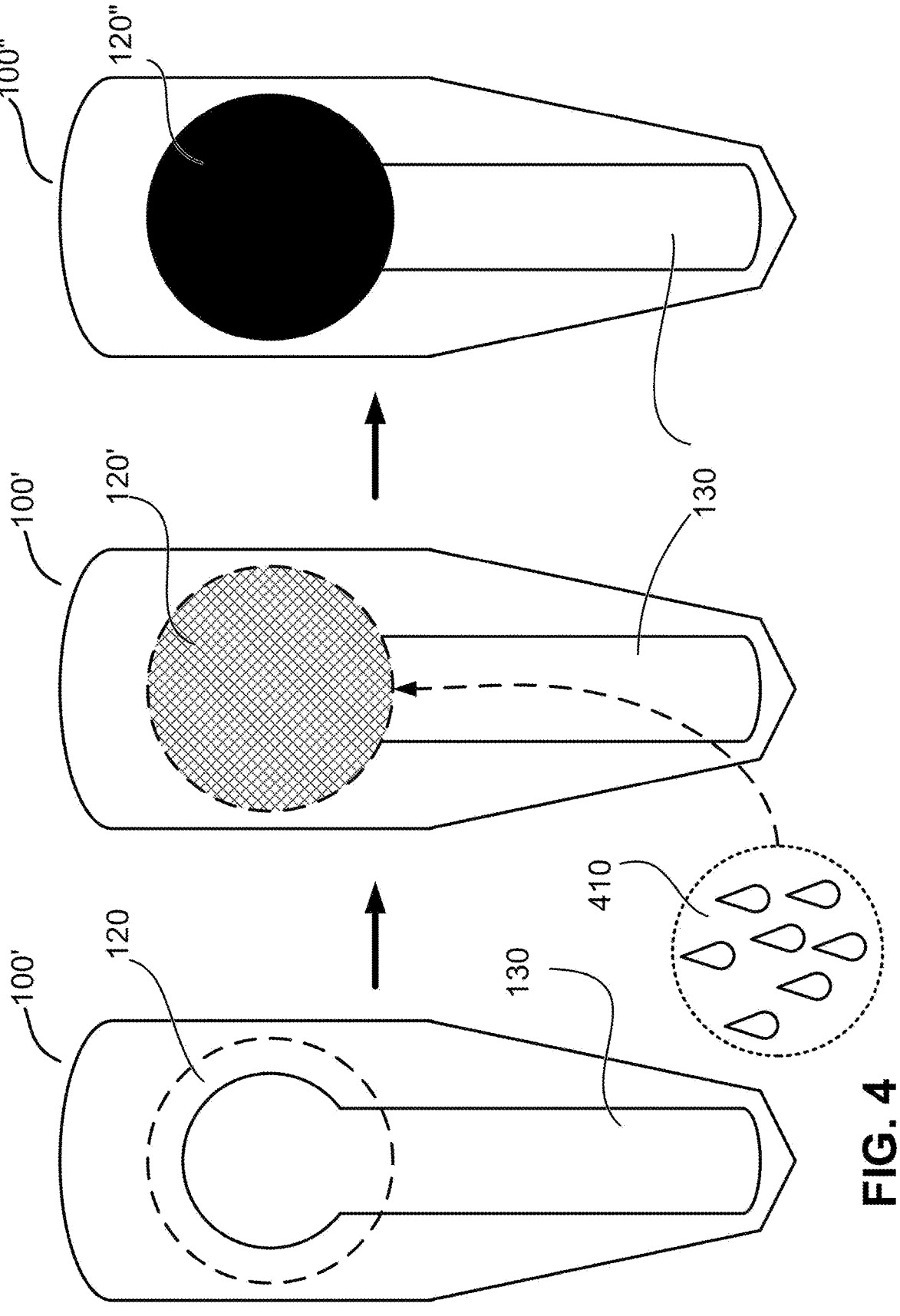
FIG. 4 depicts the color change process of an environmentally sensitive plant tag with a hydrochromic ink indicia responding to moisture exposure.

FIG. 4 illustrates the state change process of the hydrochromic tag 100 of FIG. 1. In an initial, inactivated state, the hydrochromic indicia 120 of hydrochromic tag 100 has a first color indicating that the tag has not come into contact with moisture. In first activated state, as moisture 410 is introduced via the wicking material 130, the hydrochromic indicia 120' of hydrochromic tag 100' exhibits a change of color, indicating that a first moisture level threshold has been reached. In a second activated state, the hydrochromic indicia 120" of hydrochromic tag 100" exhibits another change of color, indicating that a second moisture level threshold has been reached. According to some embodiments the second color may be the same as the first color, but with a different level of color saturation. In other embodiments, the second color may be entirely distinct from the first color.

Figure 5A:
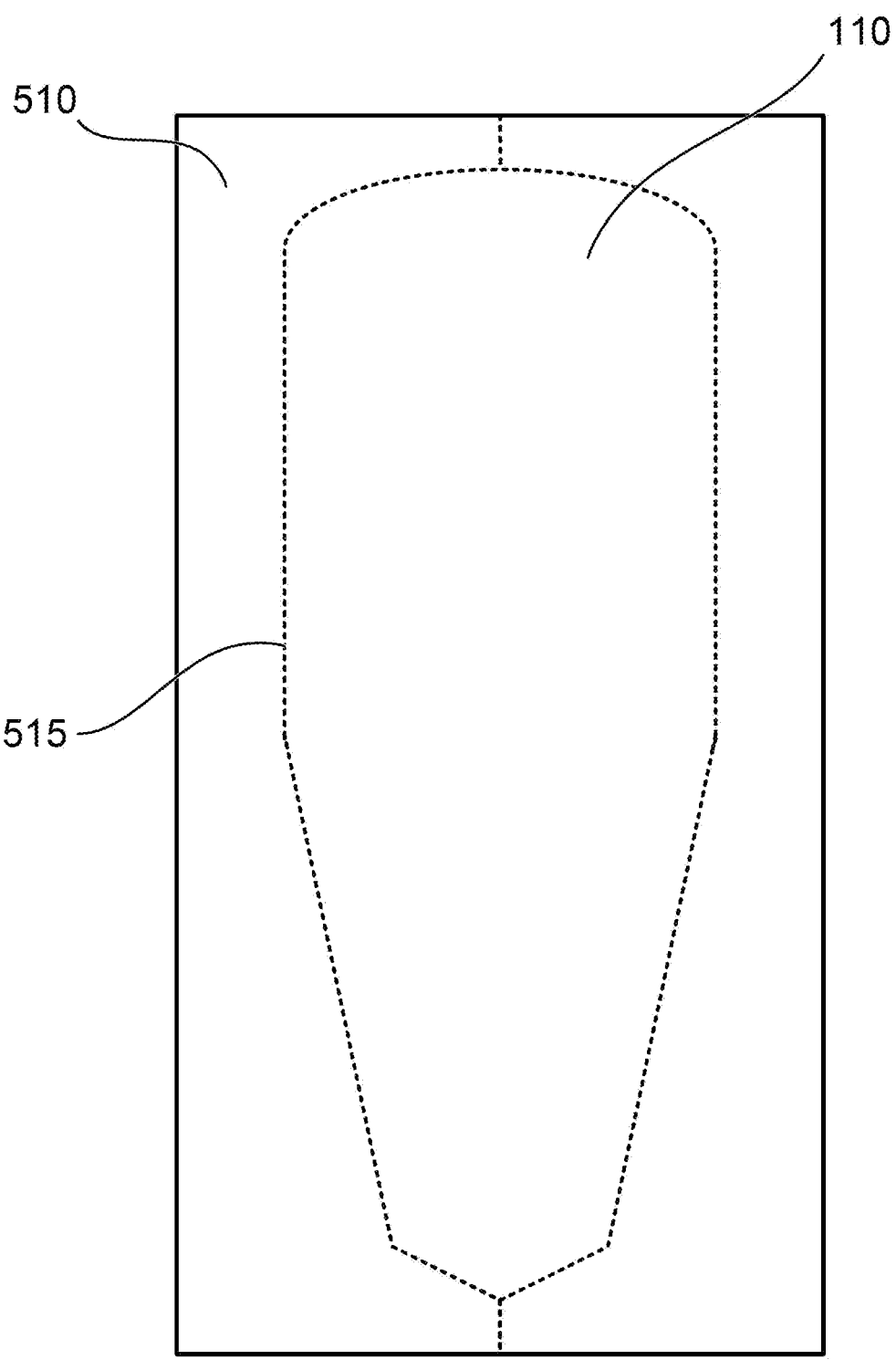
FIG. 5A shows an example embodiment of a substrate formed by scoring a sheet of substrate material.

FIG. 5A depicts an example of environmentally sensitive plant tags (e.g., tags 100, 200, 250) configured as items of manufacture. FIG. 5A illustrates that the substrate 110 is formed from a larger section of substrate material 510 and is defined by a line of weakness 515. It will be appreciated that this could include any conventional approach to forming lines of weakness on a substrate, e.g., scoring, perforation, embossed indentations, perforations, laser etching, or partial cuts. This configuration provides for ease of large scale manufacturing of the humidity sensing plant tags. The items of manufacture may be configured to be RFID tags 200 or hydrochromic tags 100.

Figure 5B:
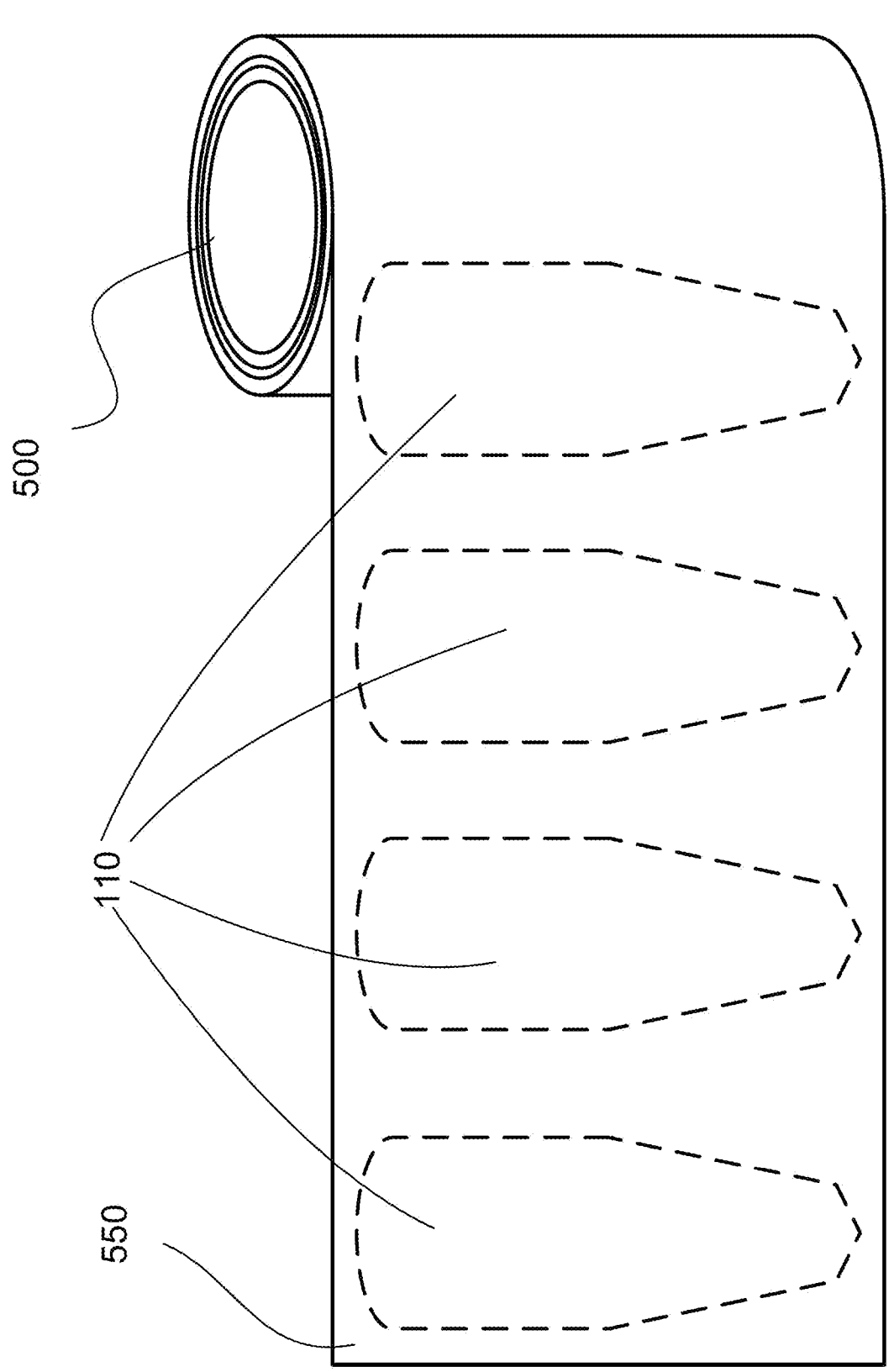
FIG. 5B shows substrates scored into a roll of substrate material.

FIG. 5B illustrates a similar embodiment, in which many substrates 110 are formed in a web of material 550, which may be formed into a roll 500, configured for continuous printing, assembly or manufacturing purposes. It will be appreciated that additional lines of weakness across the width of the web may also be provided, to allow separation of individual sections containing one or more indicators.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any manner. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The claimed invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain manner is configured in at least that manner, but may also be configured in manners that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separately claimed subject matter.

The invention claimed is:

1. An environmentally sensitive tag for use in a plant growing medium, comprising;

a substrate including a tag insertion end which is narrowed, pointed, or rounded to facilitate insertion of the tag insertion end in the plant growing medium;

an indicator located on or in the substrate and spaced away from the tag insertion end, wherein:

the indicator comprises a hydrochromic ink, the indicator has an initial state and at least one activated state, the indicator is configured to transition from the initial state to the at least one activated state in response to exposure to moisture, producing an observable change, wherein the observable change includes a change in color state of the hydrochromic ink from an initial color state to at least one activated color state and the change in color state comprises a change of at least one property chosen from the group consisting of hue, chroma, transparency, opacity, and combinations thereof; and a wicking material disposed longitudinally along or in the substrate, from an area of the substrate proximate the tag insertion end to the indicator and configured to conduct moisture from the plant growing medium to the indicator when the tag insertion end is inserted in the plant growing medium, wherein the hydrochromic ink comprises at least one component chosen from a list consisting of: (a) a mixture of a triphenylmethane dye, an oxidizing agent, a base and a humectant, (b) a mixture of an inorganic weak acid, a triarylmethane dye, and a hygroscopic agent, (c) a mixture of copper bromide, a dye and a bromide salt, (d) a silica gel impregnated with an iron (III) salt, (e) a sugar gel containing ionic dyes, (f) a composite of porphyrin, magnesium dichloride and silica gel, (g) an inorganic polymer containing an acid-base indicator, (h) hydroxyethyl cellulose containing methylene blue and urea, (i) a composite of polyvinyl alcohol and sodium borate decahydrate, (j) lithium hydroxide, (k) calcium hydroxide, (l) potassium hydroxide, (m) sodium hydrogen carbonate, (n) magnesium hydroxide, (o) sodium thiosulfate pentahydrate, (p) sodium hydroxide, (q) cobalt nitrate, (r) copper (II) sulfate, (s) copper nitrate, (t) iron (III) sulfate, (u) iron (II) sulfate, (v) iron (II) Chloride, (w) iron (III) chloride, (x) Cobalt (II) Chloride, and (y) magnesium chloride.

2. The environmentally sensitive tag of claim 1, wherein a change from the initial state to the at least one activated state occurs in response to exposure of the indicator to a predetermined moisture level threshold in a range of 10% Relative Humidity (RH) to 100% RH.

3. The environmentally sensitive tag of claim 1, wherein the indicator has a plurality of activated states each associated with a respective moisture level threshold, the indicator entering each successive activated states in response to exposure to a respective moisture greater than the respective moisture level threshold.

4. The environmentally sensitive tag of claim 3 wherein each of the plurality of activated states has a corresponding observable change that is distinguishable from the initial state and other activated states.

5. The environmentally sensitive tag of claim 2, wherein the observable change of the indicator from the initial state to the activated state is not reversed when a moisture level returns below the predetermined moisture level threshold.

6. The environmentally sensitive tag of claim 3, wherein the hydrochromic ink passes through a series of color states in response to different humidity levels, where each color state corresponds to a respective activated state of the plurality of activated states.

7. The environmentally sensitive tag of claim 1, wherein the indicator is reversible, so that when the indicator is in the activated state, the indicator is operable to revert from the activated state to the initial state in response to a moisture level falling below a predetermined minimum threshold.

8. The environmentally sensitive tag of claim 1, wherein the hydrochromic ink forms an indicia that is visible when the indicator is in the initial state and which becomes invisible when the indicator transitions to the at least on activated state; or is invisible when the indicator is in the initial state and which becomes visible when the indicator transitions to the at least one activated state.

9. The environmentally sensitive tag of claim 1, further comprising a plurality of different hydrochromic inks, each hydrochromic ink having a respective moisture level threshold and a respective observable change when the indicator is exposed to a moisture level above the respective moisture level threshold.

10. The environmentally sensitive tag of claim 1, wherein the hydrochromic ink comprises the mixture of the triphenylmethane dye, the oxidizing agent, the base and the humectant.

11. The environmentally sensitive tag of claim 1, wherein the wicking material comprises at least one component from a list consisting of woven polyester, nonwoven polyester, polyamide and blended elastane and polyester, carbon fiber, Teslin synthetic paper, polyethylene, polypropylene, polytetrafluoroethylene, and woven nylon.

12. The environmentally sensitive tag of claim 1, wherein the substrate is formed entirely or in part by the wicking material.

13. The environmentally sensitive tag of claim 1, further comprising additional material which is a same material as the substrate, at least partially surrounding the environmentally sensitive tag, and which is connected to the substrate by a line of weakness.

14. An article of manufacture, comprising a plurality of environmentally sensitive tags of claim 1 forming a connected web or sheet.

15. The article of claim 14 wherein adjacent environmentally sensitive tags in the connected web or sheet have a line of weakness along a boundary in between the adjacent environmentally sensitive tags.

16. The article of claim 15 wherein the line of weakness is selected from the group consisting of a fold, a score line, and a perforated line.

17. An environmentally sensitive tag for use in a plant growing medium, comprising;

a substrate including a tag insertion end which is nar-rowed, pointed, or rounded to facilitate insertion of the tag insertion end in the plant growing medium;

an indicator component located on or in the substrate and spaced away from the tag insertion end, having an initial state and at least one activated state, the indicator configured to transition from the initial state to the at least one activated state in response to exposure to moisture producing an observable change, wherein the indicator component changes an electrical property when it transitions from the initial state to the at least one activated state;

a wicking material disposed longitudinally along or in the substrate, from an area of the substrate proximate the tag insertion end to the indicator component and con-figured to conduct moisture from the plant growing medium to the indicator component when the tag insertion end is inserted in the plant growing medium; and an RFID tag which includes or is electrically connected to the indicator component, wherein the RFID tag is configured to change an output in response to the change in the electrical property of the indicator com-ponent.

18. The environmentally sensitive tag of claim 17, wherein the change in the electrical property of the compo-nent comprises a change in capacitance.

19. The environmentally sensitive tag of claim 18, wherein the change in capacitance increases with greater exposure to moisture.

20. The environmentally sensitive tag of claim 18, wherein the change in capacitance causes a change in a frequency of a transmission of the RFID tag.

21. The environmentally sensitive tag of claim 17, wherein the RFID tag and the wicking material are disposed inside the substrate or between the substrate and a second layer or inside of the substrate, so that the wicking material and RFID tag are substantially insulated from moisture contact, except for moisture which is transmitted from the tag insertion end through the wicking material.

22. The environmentally sensitive tag of claim 17, further comprising:

a visual indicator located on or in the substrate and spaced away from the tag insertion end, wherein the visual indicator has an initial state and at least one activated state, and is configured to transition from the initial state to the at least one activated state in response to exposure to moisture, producing a visually observable change in color state.

23. The environmentally sensitive tag of claim 17, wherein the RFID tag is configured to change the output responsive to the change in the electrical property by chang-ing data transmitted in the output.

* * * * *